United States Patent
Haurum et al.

(10) Patent No.: US 6,849,259 B2
(45) Date of Patent: Feb. 1, 2005

(54) POLYCLONAL ANTIBODY COMPOSITION FOR TREATING ALLERGY

(75) Inventors: John S. Haurum, Copenhagen (DK); Kirsten Drejer, Vaerlose (DK); Ulrik Gregers Winther Morch, Copenhagen (DK)

(73) Assignee: Symphogen A/S, Lyngby (DK)

( * ) Notice: Subject to any disclaimer, the term of this patent is extended or adjusted under 35 U.S.C. 154(b) by 0 days.

(21) Appl. No.: 09/866,573

(22) Filed: May 25, 2001

(65) Prior Publication Data

US 2002/0009453 A1 Jan. 24, 2002

Related U.S. Application Data

(60) Provisional application No. 60/211,981, filed on Jun. 16, 2000.

(51) Int. Cl.⁷ ............................................. A61K 39/395
(52) U.S. Cl. ............................... 424/171.1; 424/133.1; 424/177.1
(58) Field of Search ........................... 424/133.1, 177.1

(56) References Cited

U.S. PATENT DOCUMENTS

| | | | |
|---|---|---|---|
| 4,683,195 A | | 7/1987 | Mullis et al. .................. 435/6 |
| 4,740,371 A | * | 4/1988 | St. Remy et al. |
| 5,458,135 A | | 10/1995 | Patton et al. .......... 128/200.14 |
| 5,670,626 A | | 9/1997 | Chang .................... 530/388.5 |
| 5,789,208 A | | 8/1998 | Sharon .................... 435/91.41 |
| 5,797,392 A | | 8/1998 | Keldmann et al. ..... 128/203.15 |
| 5,939,598 A | | 8/1999 | Kucherlapati et al. ........ 800/25 |

FOREIGN PATENT DOCUMENTS

| | | | |
|---|---|---|---|
| WO | WO 96/09085 | 3/1996 | .......... A61M/15/00 |
| WO | WO 98/10776 | 3/1998 | .......... A61K/35/58 |

OTHER PUBLICATIONS

Roitt et al. (Immunology, Harper and Row, Publishers, New York, 1989, pp. 5.5–5.6 and 3.8).*

Franco M. Piazza et al. "Immunotherapy of Respiratory Syncytial Virus Infection in Cotton Rats (*Sigmodon fulviventer*) Using IgG in a Small–Particle Aerosol", *The Journal of Infectious Diseases 1992;* 166; 1422–4.

David E. Bice et al. "Animal Models of Asthma: Potential Usefulness for Studying Health Effects of Inhaled Particled", *Inhalation Toxicology*, 12:829, 2000.

Jürgen Schwarze et al. "Antigen–specific Immunoglobulin–A Prevents Increased Airway Responsiveness and Lung Eosinophilia after Airway Challenge in Sensitized Mice", *Am J Repir Crit Care Med,* vol. 158. pp 519–525, 1998.

Wayne R. Gombotz et al. "The Stabilization of a Human IgM Monoclonal Antibody with Poly (vinylpyrrolidone)", *Pharmaceutical Research,* vol. 11, No. 5, 1994.

Alan R. Brown et al. "Chamber for testing metered–dose propellant–driven aerosols of immunologically relevant proteins", *Journal of Immunological Methods,* 176 (1994) 203–212.

Mehdi Paborji et al. "Chemical and Physical Stability of Chimeric L6, a Mouse–Human Monoclonal Antibody", *Pharmaceutical Research,* vol. 11, No. 5, 1994.

Kazuo Maruyama et al. "Targetability of novel immunoliposomes modified with amphipathic poly (ethylene glycol) s conjugated at their distal terminals to monoclonal antibodies", *Biochimica et Biophysica Acta* 1234 (1995) 74–80.

Alan R. Brown "Propellant–Driven Aerosols of Ptoteins", *Acrosol Science and Technology* 24:45–56 (1996).

Visco et al., J. Immunol., 1996; 157:956–962.

De Lalla et al., Mol. Immunol., 1996; 33:1049–1058.

Urbanek et al., Clin. Allergy, 1986; 16:317–322.

Bousquet et al., J. Allergy Clin. Immunol., 1987; 79:947–954.

* cited by examiner

Primary Examiner—Patrick J. Nolan
(74) Attorney, Agent, or Firm—Clark & Elbing, LLP; Kristina Bieker-Brady, P.C.

(57) ABSTRACT

A pharmaceutical composition for treating allergy is described. The composition comprises as an active ingredient a recombinant polyclonal antibody or a mixture of different monoclonal antibodies capable of reacting with or binding to an allergen together with one or more pharmaceutically acceptable excipients. The composition may be used topically as a solution, dispersion, powder, or in the form of microspheres. The polyclonal antibody is preferably a recombinant polyclonal antibody produced by phage display technology. The pairing of specific immunoglobulin variable region light chain and heavy chain maintained from the original polyclonal immune response or selected by panning using the allergen in question is preferably maintained by bulk transfer of the pairs into an expression vector.

25 Claims, No Drawings

POLYCLONAL ANTIBODY COMPOSITION FOR TREATING ALLERGY

CROSS REFERENCE TO RELATED APPLICATIONS

This application claims priority under 35 U.S.C. §119(e) from U.S. Provisional Application No. 60/211,981, filed Jun. 16, 2000, the entire disclosure of which is incorporated by reference therein.

FIELD OF INVENTION

The present invention relates to a composition comprising a recombinant polyclonal antibody or a mixture of different monoclonal antibodies or an isolated or purified polyclonal antibody capable of reacting with or binding to an allergen, as well as the use of a polyclonal antibody capable of reacting with or binding to an allergen for the treatment of allergy.

BACKGROUND OF THE INVENTION

The protective effects of humoral immunity are known to be mediated by a family of structurally related glycoproteins called antibodies. Antibodies initiate their biological activity by binding to antigens. Antibody binding to antigens is generally specific for one antigen and the binding is usually of high affinity. Antibodies are produced by B-lymphocytes. Blood contains many different antibodies, each derived from a clone of B-cells and each having a distinct structure and specificity for antigen. Antibodies are present on the surface of B-lymphocytes, in the plasma, in interstitial fluid of the tissues and in secretory fluids such as saliva and mucus on mucosal surfaces.

All antibodies are similar in their overall structure, accounting for certain similarities in physiochemical features such as charge and solubility. All antibodies have a common core structure of two identical light chains, each about 24 kilodaltons, and two identical heavy chains of about 55–70 kilodaltons each. One light chain is attached to each heavy chain, and the two heavy chains are attached to each other. Both the light and heavy chains contain a series of repeating homologous units, each of about 110 amino acid residues in length which fold independently in a common globular motif, called an immunoglobulin (Ig) domain. The region of an antibody molecule formed by the association of the two heavy chains is hydrophobic. Antibodies are known to cleave at the site where the light chain attaches to the heavy chain when they are subjected to adverse physical or chemical conditions. Because antibodies contain numerous cysteine residues, they have many cysteine—cysteine disulfide bonds. All Ig domains contain two layers of beta-pleated sheets with three or four strands of anti-parallel polypeptide chains.

Despite their overall similarity, antibody molecules can be divided into distinct classes and subclasses based on phys-iochemical characteristics such as size, charge and solubility, and on their behavior in binding to antigens. In humans, the classes of antibody molecules are: IgA, IgD, IgE, IgG and IgM. Members of each class are said to be of the same isotype. IgA and IgG isotypes are further subdivided into subtypes called $IgA_1$, $IgA_2$ and $IgG_1$, $IgG_2$, $IgG_3$ and $IgG_4$. The heavy chains of all antibody molecules in an isotype share extensive regions of amino acid sequence identity, but differ from antibodies belonging to other isotypes or subtypes. Heavy chains are designated by the letters of the Greek alphabet corresponding to the overall isotype of the antibody molecule, e.g., IgA contains α, IgD contains δ, IgE contains ε, IgG contains γ, and IgM contains μ heavy chains. IgG, IgE and IgD circulate as monomers. IgA molecules secreted through the epithelia into the mucosal lining of body cavities are homodimers whereas IgM molecules are pentamers. Circulating IgA exists mainly as a monomer. Multimeric forms of IgA and IgM are both stabilized by the so-called J chain. Secreted IgA (S-IgA) is produced by B cells residing in lamina propria and taken up by epithelial cells on the basolateral side through the poly-immunoglobulin receptor (pIgR), transported through the epithelial cell and secreted into the mucosa on the luminal side. When the IgA:J chain:pIgR complex is released, the pIgR is cleaved by a protease and a part of the pIgR molecule called the secretory component (SC) remains bound to the IgA:J chain complex. Thus, S-IgA is a complex consisting of IgA, the J chain, and the SC of which the two latter are covalently bound to the IgA molecule through disulphide bonds. S-IgA is very resistant to the proteolytic environment of the epithelial mucosa e.g. in the respiratory or the gastrointestinal tract, and as such make up the primary specific immune system in these sites. It has been demonstrated that S-IgA has an immunomodulating effect and may induce tolerance to the antigens they bind.

There are between $10^8$ and $10^{10}$ structurally different antibody molecules in every individual, each with a unique amino acid sequence in their antigen combining sites. Sequence diversity in antibodies is predominantly found in three short stretches within the amino terminal domains of the heavy and light chains called variable (V) regions, to distinguish them from the more conserved constant (C) regions.

Immunoglobulin E (IgE) is responsible for so-called type 1 hypersensitivity which manifest itself as common diseases such as allergic rhinitis, allergic conjunctivitis, hay fever, allergic (extrinsic) asthma, bee venom allergy, and food allergy. Allergen-specific IgE is produced in excess in patients with IgE-mediated allergies. IgE circulate in the blood and bind to high-affinity Fc receptors for IgE on basophils and mast cells in blood, various tissues, or on mucosal surfaces. In most allergic responses, the allergens enter the body of a patient through inhalation, ingestion, or through the skin. The allergen molecules bind to preformed IgE already bound to the high-affinity receptor FcεRI on the surfaces of mast cells and basophils, resulting in the crosslinking of several IgE molecules and triggering the release of histamine and other inflammatory mediators causing the various allergic symptoms.

Among the tissues that are most susceptible to local IgE-mediated allergic reactions are the conjunctiva, the mucosa of the nasal cavity or the oropharynx (allergic rhinitis), the mucosal linings of the bronchial tract, and the gastrointestinal mucosa. Thus, allergens enter the respiratory tract through inhalation and get trapped on the mucosal surfaces of the nasal lining or the bronchial passages of the respiratory tract. Airborne allergens also get in contact with moist surfaces of eyes and ears and are retained on the mucosa. The mucosal tissues are densely populated with mast cells and allergens arriving at these sites may therefore bind IgE and activate mast cells.

The therapeutic principles and treatment modalities in the management of allergy have not changed substantially in recent years. Immunosuppressive drugs such as steroids for suppressing immune activities and bronchial dilators for relieving asthma symptoms have long been the main treatment modality for patients with allergic asthma. Desensitization immunotherapy is the most important novel therapy for severely affected patients, but the medical advances have been limited to refining the classification of the allergenic substances, improving diagnostic methods, and providing a better controlled and broader library of allergen extracts for immunotherapy. As for research, progress has been made in the identification and isolation of major allergenic components of allergenic substances. For example, the major allergic components of ragweed, house dust mites, and cat and dog dander and saliva have been identified. When the allergen particles, e.g. timothy grass pollen arrive to the airway mucosa they disintegrate into major and minor allergic components.

Antibodies have been suggested for a number of clinical treatments: Medimmune Inc. is studying the use of humanized anti-respiratory syncytial virus (RSV) monoclonal antibodies and markets a polyclonal anti-RSV human immunoglobulin product (RespiGam) isolated from human donor blood and used to treat RSV infection. Medimmune also markets CytoGam, an anti-CMV (*cytomegalovirus*) human immunoglobulin for the treatment of CMV infection. IDEC and Genentech are jointly performing clinical trials of a chimeric mouse-human monoclonal antibody (Rituximab) aimed at the CD20 antigen found on mature B cells and most non-Hodgkin's lymphoma tumors for the treatment of relapsed or refractory low-grade non-Hodgkin's lymphoma. GalaGen is studying the use of bovine polyclonal immunoglobulin (Diffistat-G) for treatment of *Clostridium difficile* antibiotic associated diarrhea. SmithKline Beecham and Schering-Plough are developing an anti-IL-5 monoclonal antibody which has been shown in clinical trials to prevent eosinophilic inflammation and airway constriction. An anti-IgE monoclonal antibody is being developed by Genentech to "switch-off" allergies. The antibody Rhu-Mab-E25, which is a humanized chimeric IgG, monoclonal antibody specific for a unique epitope on human high affinity IgE receptors (FceRI), has been shown to reduce free IgE levels after the first administration by injection. It attenuated both early and late phase responses to inhaled allergens after multiple injections. Examples of antibodies used therapeutically also include a nebulized IgG (Sandoz), which is used intranasally against RSV; HNK20 (Oravax), an anti-RSV IgA; and 4B9 (Bristol Myers-Squibb), an anti-group B *Streptococcus* IgM monoclonal antibody Other therapeutically useful monoclonal antibodies include monoclonal anti-CD4 antibodies, anti-IL-2 antibodies and anti-IL-4 antibodies.

The immunotherapy of RSV infection using small particle aerosols of IgG has been disclosed by Piazza et al. (J. Infect. Dis., Vol. 166, pp. 1422–1424, 1992). In this study it was shown that a 15-minute exposure to an aerosolized 5% solution of IgG effected a 50-fold reduction in pulmonary virus. Brown (Aerosol Science and Technology, Vol. 24, pp. 45–56, 1996) discloses the use of antibodies as inhibitors or antagonists of cytokines to depress respiratory inflammatory diseases or allergen-induced asthmatic responses. Also mentioned is local respiratory delivery of pathogen-specific antibody for treatment of acute viral or bacterial respiratory infections.

Antibody liposomes, i.e., immunoliposomes, are disclosed by Maruyama et al. (Biochim. Biophys. Acta, Vol. 1234, pp. 74–80, 1995). Coating liposomes with antibody leads to enhanced uptake of the liposome by the reticuloendothelial system. Human monoclonal antibodies are known to be useful as anti-tumor agents. A mouse/human monoclonal IgG antibody specific for the Lewis Y antigen found on the surface of tumor cells is disclosed by Paborji et al. (Pharmaceutical Research, Vol. 11, No. 5, pp. 764–771, 1994). The use of antibodies in metered-dose propellant driven aerosols for passive antibody aerosol therapy against respiratory infections is suggested in Brown et al. (Journal of Immunological Methods, Vol. 176, pp. 203–212, 1994). Immune responses in the respiratory tract are of great importance for protection against infections of the respiratory system and for their involvement in respiratory allergies and asthma. Effective targeting of immunomodulating reagents including monoclonal antibodies to the respiratory tract is shown to be of benefit in increasing local immunity to respiratory pathogens or decreasing immune-mediated respiratory pathology. Inhaled immunoconjugates, immunoliposomes or immunomicrospheres have application in the lung as killers of cancer cells; (immunoconjugates) or, in the case of immunoliposomes and microspheres, as stealth delivery particles of a variety of therapeutic agents. An IgM anti-group B *Streptococcus* monoclonal antibody is disclosed by Gombotz et al. (Pharmaceutical Research, Vol. 11, pp. 624–632, 1994).

U.S. Pat. No. 5,670,626 proposes the use of monoclonal antibodies for the treatment of IgE-mediated allergic diseases such as allergic rhinitis, allergic asthma and allergic conjunctivitis by employing monoclonal antibodies to inhibit the entry of allergenic molecules into mucosal tissues. The binding of allergenic molecules by antibodies is assumed to inhibit the allergens from being taken up by mucosal epithelial cells In certain clinical situations, the use of monoclonal antibodies is associated with specific disadvantages. Thus, monoclonal antibodies are directed against single antigenic epitopes. Therefore, if the target is of a complex nature presenting many different epitopes then the functional avidity of the monoclonal antibody may be low or lowered below a critical threshold allowing the target to escape elimination through immune recognition.

Also, because monoclonal antibodies are directed against single antigenic determinants, the density of the antibody targets on e.g. allergens may not be high enough to mediate elimination of the allergen. The efficient activation of complement similarly requires high target antibody densities which may not be achieved with single specificity monoclonal antibodies.

Thus, in the case of allergens, monoclonal antibodies are sub-optimal as they are directed against single epitopes. The majority of allergens are complex proteins, consisting of many protein and peptide epitopes, and existing in many variants. Thus, a single monoclonal antibody preparation cannot be expected to exhaustively cover more than a minority of the possible epitopes on an allergen, e.g. a pollen particle or proteins from cat dander. This means that if the desired clinical effect of an antibody can be characterized as a complete blocking of the available antibody epitopes, then a single monoclonal antibody will not be sufficient. Further, it an antibody preparation should preferably be developed against several homologous allergens from closely related allergens, e.g. pollens, or against several proteins from one allergen source e.g. animal dander, then a single monoclonal antibody will not meet the required efficacy.

Nevertheless, a paper by Schwarze and coworkers (Am. J. Resp. Crit. Care Med. Vol. 158, pp. 519–525, 1998) investigated the therapeutic efficacy of a monoclonal antibody directed against the major ragweed allergen Amb a I in a murine allergy model based on mice (Balb/c) sensitized and challenged with both Amb a I and whole ragweed extracts. It was demonstrated that administration of the monoclonal IgA antibody before allergen exposure decreased airway responsiveness to metacholine challenge, and decreased the number of pulmonary eosinophils and Amb a I-specific IgE levels in serum. Moreover, the study indicate that administration of IgA had an immunomodulatory effect implying that IgA treatment could have a long-term desensitizing effect on allergy. However, it must be stressed that this allergen model is based on the induction of allergy-like symptoms using a single allergen, Amb a I. Thus, the study does not take into account that the vast majority of allergies are caused by reactions towards a number of allergen proteins and epitopes derived from a single allergen particle, which emphasizes the need for a polyclonal antibody mixture in this regime of treatment. Furthermore, human allergy is profoundly more complex than the allergy-like symptoms induced in an inbred mouse strain (Inhal. Toxicol., Vol 12, pp. 829–62, 2000). Consequently, the potential usefulness of monoclonal antibodies as allergen blocking agents is limited. Finally, monoclonal antibodies may display cross-reactivity to antigenic structures of host cell tissue resulting in potential unwanted side effects. When this occurs the cross-reactivity cannot be removed by adsorption. Therefore a large number of different monoclonal antibodies may need to be produced in order to generate the desired combination of antigen specificity and target selectivity, and even so there still remains a significant risk of cross-reactivity towards endogenous self-antigens in a proportion of patients.

A separate issue is the generation of human anti-mouse antibody responses (HAMA). Conventional murine monoclonal antibodies are foreign proteins to the human recipient, and therefore a HAMA immune response is often elicited in the recipient, which may lead to unwanted side effects in addition to reduced treatment efficacy. In order to circumvent this problem, chimeric monoclonal antibodies possessing human constant (C) regions and murine variable (V) regions have been developed. Furthermore humanized monoclonal antibodies, where only the hypervariable complementarity determining region (CDR) is derived from mouse monoclonal antibodies and finally, so-called fully human monoclonal antibodies produced in mice transgenic for human immunoglobulin genes have been developed to avoid these problems. However, a potential for the generation of anti-idiotype antibody responses specific for the V-region specificity determining CDR still exists when injecting large amounts of monoclonal antibodies with identical V-regions.

For these reasons as outlined above, it may often be preferable to use polyclonal antibodies.

In WO 98/10776 it is theorized that phospholipase $A_2(PLA_2)$ is involved in the pathogenesis of many diseases acting as an inflammatory mediator promoting chronic inflammation. Thus it is suggested to use serum reactive with at least one phospholipase $A_2$ enzyme for the treatment of neoplasms in mammals. There is no suggestion to use polyclonal antibodies for blocking the uptake of an allergen by topical administration of an antibody binding to the allergen.

U.S. Pat. No. 4,740,371 describes a modification of allergen immunotherapy whereby an immune complex of the allergen and an antibody thereto is used for desensitization treatment, the antibody being present in molar excess with respect to the allergen to prevent an anaphylactic response. The purpose of the inclusion of the antibody in this treatment is to decrease the risk of allergic side effects such as anaphylactic shock to the desensitization treatment. The proportion of antibody to be added to the allergen is defined essentially by the neutralizing power of the antibody. Enough antibody must be used so that when the composition is administered, there is practically no allergic effect induced by the allergen. The adding of antibody to the allergen composition is solely a remedy to avoid side effects of the allergen exposure, the treatment still being an allergen immunotherapy.

There are several drawbacks of using conventional polyclonal antibodies in the treatment of allergy. First of all, polyclonal antibodies in the form of IgG purified from hyperimmune human serum is available in limited supply and in amounts insufficient for the treatment of allergic diseases and other common conditions. Also, gamma globulin preparations are expensive to produce, and display low efficacy due to their mixed nature containing an overwhelming majority of non-specific human serum immunoglobulin reactivities. Also, there exist a real risk of transmitting contaminating reagents, including infectious microorganisms (hepatitis virus, HIV, prions, others), or mitogens, cytokines and toxins. Finally, the variability between preparations remains a major problem. In order to solve the problem of supply, xenogeneic sources of polyclonal antibodies including serum from immunized non-human animals have been tested. However, such compositions may result in the generation of potent anti-xenoantibody responses, and carries a real risk of serious side effects such as anaphylactic shock or serum sickness, as well as the transmission of xenotropic infections.

U.S. Pat. No. 5,789,208 describes the use of a recombinant polyclonal antibody for vaccine therapy and prophylaxis to treat or prevent neoplastic diseases. The antibodies are used for boosting a patient's immune system for the possible later recognition of the antigen to which the antibody binds and thereby initiate an elimination reaction. The vaccination will have to be repeated to be effective. There is no suggestion to use polyclonal antibodies reacting with or binding to allergens in allergy treatment where the polyclonal antibodies should be administered completely differently before, during, or shortly after the patient has been exposed to an allergen.

SUMMARY OF THE INVENTION

Accordingly, the present invention relates to a pharmaceutical composition comprising as an active ingredient a recombinant polyclonal antibody or a mixture of different monoclonal antibodies or an isolated or purified polyclonal antibody capable of reacting with or binding to an allergen together with one or more pharmaceutically acceptable excipients.

In most embodiments, the pharmaceutical composition according to the invention is free of the allergen to which the recombinant polyclonal antibody or the mixture of different monoclonal antibodies or the isolated or purified polyclonal antibody bind or is reactive with. However, in special cases during so-called specific allergen immunotherapy to induce allergen tolerance in a patient, the allergen-specific polyclonal antibody may be administered to the patient in conjunction with an allergen preparation, in order to enable or enhance the efficacy of the tolerance induction procedure.

In another aspect, the invention relates to the use of a polyclonal antibody with desired specificities for the manufacture of a pharmaceutical composition for the prophylaxis or treatment of allergy or allergic conditions such as allergic rhinitis, allergic conjunctivitis, hay fever, asthma, etc.

In a further aspect, the invention relates to a method of preventing or treating allergy, which comprises administering to a patient in need thereof a sufficient amount of a polyclonal antibody capable of reacting with or binding to an allergen to which the patient has shown an allergic reaction.

The use of a polyclonal antibody has potential clinical advantages compared with the use of a monoclonal antibody due to the presence of multiple reactivities in a polyclonal antibody against the allergen-target in question. There may be generated a polyclonal antibody which has reactivities against all epitopes on a complex allergen target. Due to the polyclonal nature of the composition, containing many epitope specificities, the functional antibody density which can be achieved on complex allergen antigens when using a polyclonal antibody is significantly higher, than with a monoclonal antibody. This results in more efficient blocking or clearance of the target allergen. Further, the polyclonal nature of the composition enables recognition of and blocking of epitopes on related, homologous allergen isotypes, due to broad reactivity with several epitopes shared in part between related allergens, something which is not enabled by a monoclonal antibody.

Further, it can be expected that treatment with allergen-specific polyclonal antibodies of the IgA or IgG isotype will have an immunomodulating effect by inducing tolerance to an allergen, and thus have a long term effect in curing the allergy or reducing the need for further treatment. Thus, a further aspect of the invention relates to the use of a pharmaceutical composition according to the invention for prophylactic treatment inducing tolerance to the allergen. This may even be used in patients where an allergic reaction has not yet been observed but which patients due to family history or genetic analysis are likely to develop allergy to an allergen.

Furthermore, contrary to a monoclonal antibody, a polyclonal antibody preparation comprises a mixture of specificities, and therefore any single and individual, cross-reacting specificity idiotype will be delivered at a very low concentration, thus reducing significantly the potential for harmful side-effects, due to cross-reactivity. In other words, the potential for deleterious side-effects due to unwanted tissue cross-reactivity is diluted out in the polyclonal antibody reagent. Further, any unwanted cross-reactivity of the polyclonal antibody preparation can be removed by adsorption. If a monoclonal antibody results in an unwanted cross-reactivity, it is inherent to the single antibody present and can of course not be removed without destroying the activity of the preparation.

Also, in analogy with the properties of polyclonal antibodies in terms of the diminished potential for cross-reactivity, polyclonal antibodies will also be much less likely than monoclonal antibodies to induce a neutralizing anti-idiotype immune response, since each single epitope-specific idiotype of the administered polyclonal antibody preparation is present in a very low quantity or concentration, being below the threshold for generation of an anti-idiotype response.

Some of the drawbacks of using conventional polyclonal antibodies in the form of IgG purified from hyperimmune human (limited supply, expensive to produce) or serum from normal animals (anti-xeno-antibody responses, anaphylactic shock) is the use of serum or other biological material from animals transgenic for human immunoglobulin genes. Thus, such animals can be immunized with allergens, and used as a source to isolate allergen-specific polyclonal antibody products of fully human sequence.

The immune complexes on the nasal linings will be cleared as the mucous excretion is swallowed. The immune complexes on the mucosal surfaces of the tracheal and bronchial airways will be expelled into the mouth, mixed with saliva, swallowed and digested in the gastrointestinal tract. In order to achieve betters effects in adsorbing and clearing allergenic molecules from the mucous fluids on the mucosal surfaces and preventing any uptake of the complexed allergen by the mucosal epithelial cells, the allergen-specific antibody can be conjugated to polymer backbones or microbeads forming microspheres.

Thus the pharmaceutical composition according to the invention may be formulated as a solution, dispersion, powder, or in form of microspheres.

DETAILED DESCRIPTION OF THE INVENTION

The term "antibody molecule" describes the single antibody protein molecule or fragments thereof containing one or more variable antigen binding domain(s) and constant regions. An antibody molecule is usually monospecific, but may also be described as idiospecific, heterospecific, polyspecific or of unwanted specificity. It cannot be non-specific except in the sense of non-immunochemical binding. Antibody molecules bind by means of specific binding sites to specific antigenic determinants or epitopes on antigens.

Collectively, antibodies may exist as a population of molecules where a fraction or all of the members are capable of reacting with a specific antigen determinant Thus, in the present context, the term "antibody" refers to compositions/mixtures/populations of antibody molecules, such as they are found as the functional component of anti-serum or immune serum derived from mammals, or as they are found in monoclonal or polyclonal antibody compositions with similar functionality prepared either from human or animal sources or by recombinant technologies, including transgenic animals and phage display or by conventional hybridoma technology.

The term "polyclonal antibody" denotes a mixture of different antibody molecules which react with more than one immunogenic determinant of an antigen.

In the present context, the term "polyclonal antibody" encompasses a polyclonal antibody isolated or purified from mammalian blood, secretions, or other fluids, or from eggs, as well as a mixture of different monoclonal antibodies, and finally a polyclonal antibody may be produced as a recombinant polyclonal antibody.

The term "recombinant polyclonal antibody" refers to a polyclonal antibody generated by the use of recombinant technologies, and such polyclonal antibodies are hereafter named symphobodies. Thus, a symphobody contains a high concentration of different antibody molecules, all or a majority of which are displaying a desired binding activity towards an antigen composed of more than one epitope.

Symphobodies can be generated by recombinant DNA techniques followed by expression in eukaryotic cells, including yeast, fungi, insect, plant, or mammalian cells, or in prokaryotic cells such as bacteria, or as expressed from virus vectors, or through gene therapy, or from expression of transgenes in animals.

Preferably at least 85% of the antibody molecules in the symphobody preparation are target-specific, more preferably at least 90% are target-specific, even more preferably at least 95% are target-specific, and most preferably all antibody molecules in the symphobody preparation are target-specific.

By the term "a mixture of different monoclonal antibodies" is meant a mixture of two or more different monoclonal antibodies. The term "two or more" in the present context denotes from 2 to 100, preferably from 3 to 60, more preferably from 5 to 40, most preferably from 10 to 25 different monoclonal antibodies By the term "an isolated or purified polyclonal antibody" is meant a polyclonal antibody isolated or purified from mammalian blood, secretions, or other fluids, or from eggs.

It is to be understood that the expressions "an antibody, a polyclonal antibody, a recombinant antibody, a mixture of different monoclonal antibodies and an isolated or purified polyclonal antibody" all also encompasses functional fragments of the mentioned antibodies.

A currently preferred method of preparing a recombinant polyclonal antibody is by making polyclonal antibody libraries (PCAL), for instance as disclosed in U.S. Pat. No. 5,789,208 (to J. Sharon) which is hereby incorporated by reference in its entirety.

More specifically, the polyclonal antibody included in the pharmaceutical composition may be prepared by immunizing an animal, preferably a mammal, with an allergen of choice followed by the isolation of antibody-producing B-lymphocytes from blood, bone marrow, lymph nodes, or spleen. Alternatively, antibody-producing cells may be isolated from an animal and exposed to an allergen in vitro against which antibodies are to be raised. The antibody-producing cells may then be cultured to obtain a population of antibody-producing cells, optionally after fusion to an immortalized cell line such as a myeloma.

More preferably, as a starting material B-lymphocytes may be isolated from the tissue of an allergic patient, in order to generate fully human polyclonal antibodies.

The present composition may also be generated using suitable tissue from mice, rats, pigs (swine), sheep, bovine material, or other animals transgenic for the human immunoglobulin genes, as starting material in order to generate fully human polyclonal antibodies.

Particularly, in the case of mice or other animals transgenic for the human immunoglobulin genes (e.g. as disclosed in U.S. Pat. No. 5,939,598), the animals may be immunized to stimulate the in vivo generation of specific antibodies and antibody producing cells before preparation of the polyclonal antibody composition from the animal by extraction of B lymphocytes or purification of polyclonal serum.

A combinatorial library may be prepared from immunized B lymphocytes by associating $V_L$ and $V_H$ randomly in a cloning vector. Thus, the recombinant polyclonal antibody is generated under such conditions that the immunoglobulin heavy chain variable region and light chain variable region gene segments are linked together randomly in order to allow for the bulk transfer of variable region light chain and heavy chain gene pairs from one vector to another, while allowing stable pairing of specific immunoglobulin variable region light chain and heavy chain gene segments as they are present upon selection from a parental library of immunoglobulin variable region light chain and heavy chain gene segment pairs encoding antibody molecules capable of reacting with or binding to an allergen.

Single cell PCR may be used in an attempt to retain the native pairing of $V_L$ and $V_H$ in the single cell. In this case antibody-producing B-lymphocytes which have been isolated from animals or humans may be fixed with a fixative solution or a solution containing a chemical such as formaldehyde, glutaraldehyde or the like. The cells are then permeabilized with a permeabilization solution comprising for example a detergent such as Brij, Tween, polysorbate, Triton X-100, or the like. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and V, mRNA into the corresponding cDNA sequences.

Reverse transcription may be performed in a single step or optionally together with a PCR procedure, using a reverse transcriptase, sufficient quantities of the four dNTPs and primers that bind to the mRNA providing a 3' hydroxyl group for reverse transcriptase to initiate polymerization. Any primer complementary to the mRNA may be used, but it is preferred to use primers complementary to the 3'-terminal end of the $V_H$ and $V_L$ molecules so as to facilitate selection of variable region mRNA.

Upon reverse transcription, the resulting cDNA sequences may be amplified by PCR using primers specific for immunoglobulin genes and, in particular, for the terminal regions of the $V_H$ and $V_L$ nucleic acids. PCR procedures may be followed as disclosed in, e.g., U.S. Pat. No. 4,683,195. Preferably, the cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells. For example, after linking, cells can be washed in a solution of sodium dodecyl sulfate (SDS). The SDS precipitates out of the cells after incubation on ice and the supernatant can be electrophoresed into an agarose or acrylamide gel. Alternatively, or in combination with the SDS process, using a reagent such as digoxigenin-linked nucleotides, DNA products synthesized will remain within the cell and be amplified. The linked product is recovered upon electrophoresis of the supernatant.

After electrophoresis of the supernatant, the gel slice corresponding to the appropriate molecular weight of the linked product is removed and the DNA isolated on, for example, silica beads. The recovered DNA can be PCR amplified using terminal primers, if necessary, and cloned into vectors which may be plasmids, phages, cosmids, phagamids, viral vectors or combinations thereof. Convenient restriction enzyme sites may be incorporated into the hybridized sequences to facilitate cloning. These vectors may also be saved as a library of linked variable regions for later use.

The linked $V_H$ and $V_L$ region genes may be PCR amplified a second time using terminal nested primers, yielding a population of DNA fragments which encode the linked $V_H$ and $V_L$ genetic regions. The grouping of $V_H$ and $V_L$ combinations is an advantage of this process and allows for the in mass or batch transfer of all clones and all DNA fragments during this and all cloning procedures.

Preferably, the recombinant polyclonal antibody may be generated under such conditions that the immunoglobulin heavy chain variable region and light chain variable region gene segments are linked together in a head-to head orientation, in order to allow for the bulk transfer of variable region light chain and heavy chain pairs from one vector to another, including from phage to vector, and including from the cell of origin to phage or vector, resulting in a stable pairing of specific immunoglobulin variable region light chain and heavy chains gene segments as they are found in the original polyclonal immune response of the animal or human individual.

It may sometimes be desirable to treat the variable region gene sequences with a mutating agent. Mutating agents create point mutations, gaps, deletions or additions in the genetic sequence which may be general or specific, or random or site directed. Useful mutating agents include ultraviolet light, gamma irradiation, chemicals such as ethidium bromide, psoralen and nucleic acid analogs, or DNA modifying enzymes such as restriction enzymes, transferases, ligases and specific and nonspecific nucleases and polymerases. Moreover it may be feasible to use mutator strains. In particular, random mutations may be introduced in the CDRs of the $V_H$ and $V_L$ region genes by oligonucleotide directed mutagenesis. Mutations introduced into the gene sequence will ultimately increase library complexity and diversity as well as affinity for antigen which may further increase the library's usefulness in treatment. Furthermore, such mutagenesis may be used on a single $V_H$ and $V_L$ pair or on a defined group of such pairs to generate a library de novo.

Cloning is performed, for example, by cleaving the cDNA and vector sequences with a restriction enzyme, it necessary isolating certain nucleic acid fragments, mixing the fragments together in the presence of ligase in a suitable balanced salt, solution, and incubating the mixture under enzymatically acceptable conditions for a prescribed period of time. Using different enzyme recognition sites at each terminus of the cDNA, cloning orientation can be predetermined.

Vectors are transformed into suitable host cells and the cultures amplified to expand the different populations of vectors that comprise the library. Host cells for prokaryotic vectors may be a culture of bacteria such as *Escherichia coli*. Host cells for eukaryotic vectors may be a culture of eukaryotic cells such as any mammalian, insect or yeast cell lines adapted to tissue culture. Bacterial cells are transformed with vectors by calcium chloride-heat shock or electroporation, although many other transformation procedures would also be acceptable. Eukaryotic cells are transfected with calcium phosphate precipitation or electroporation, although many other transformation procedures would also be acceptable. The DNA fragments may be cloned into prokaryotic or eukaryotic expression vectors, chimeric vectors or dual vectors. The expression vector may be a plasmid, cosmid, phage, viral vector, phagemid and combinations thereof, but is preferably a phage display vector wherein the recombinant product is expressed on the phage surface to facilitate screening and selection. Useful transcriptional and translational sites may be placed on the expression vector including RNA polymerase recognition regions such as a TATA box site, a CAT site, an enhancer, appropriate splicing sites, if necessary, a AT rich terminal region and a transcription initiation site. Useful sites to facilitate translation include translational start and stop sites and ribosome binding sites. Typically, some of the more useful sites for efficient eukaryotic expression, such as the SV40, CMV, HSV or baculovirus promoter/enhancer region, are derived from viruses. The resulting recombinant antibody may be of the murine class $IgG_1$, $IgG_{2a}$, $IgG_{2b}$, IgM, IgA, IgD or IgE, the human classes $IgG_1$, $IgG_2$, $IgG_3$, $IgG_4$, IgM, $IgA_1$, $IgA_2$, IgD or IgE, or combinations or fragments thereof. Preferably, the chimeric antibody library is composed of primarily IgG antibodies or Fab antibody fragments.

Selection of a recombinant polyclonal antibody with desired specificity can be performed e.g. by affinity selection (panning) using an allergen-coated surface for binding the phage particles exhibiting a relevant antibody specificity. The majority of phages in the phage library are eliminated by washing and the bound phage particles are retrieved by harsher conditions (elution). After the selection procedures, the $V_L$ and $V_H$ antibody gene pairs in the selected library of phage particles can be subcloned into a different vector designed for expression of the recombinant polyclonal antibody as a complete antibody molecule or a fragment thereof such as a Fab fragment.

The use of recombinant DNA technology for generating a recombinant polyclonal antibody is a cost-effective way of generating antibodies, and the production of well-characterized, polyclonal antibody preparations with desired specificities, would overcome the above problems with conventional polyclonal antibody sera and individual monoclonal antibodies and allow the use of such reagents for the prophylaxis or treatment of allergy or allergic conditions, e.g. asthma.

Pharmaceutical Compositions

In a preferred embodiment, the pharmaceutical composition of the invention is one intended for topical administration/application to mucosa, such as the oropharynx, nasal cavity, respiratory tract, gastrointestinal tract, eye such as the conjunctival mucosa, vagina, urogenital mucosa, or for dermal application.

A particularly interesting use of the pharmaceutical composition is for application to the nasal, bronchial or pulmonary mucosa. Specifically, the topical treatment of allergy using inhaled polyclonal antibodies would be a particularly useful application of such reagents, allowing the discovery and development of novel therapeutic or preventive modalities which are cheap to produce, harmless and of no toxicity, and aimed towards a disease afflicting a very large proportion of the human population.

In order to obtain optimal delivery of the polyclonal antibody to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of the polyclonal antibody to the respiratory tract mucosa may be from the group consisting of a) carbohydrates, e.g., monosaccharides such as fructose, galactose, glucose. D-mannose, sorbiose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, f) polycationic polymers, such as chitosan or a chitosan salt or derivative.

Over the years certain drugs have been sold in compositions suitable for forming a drug dispersion for oral inhalation (pulmonary delivery) to treat various conditions in humans. Such pulmonary drug delivery compositions are designed to be delivered by inhalation by the patient of the drug dispersion so that the active drug within the dispersion can reach the lung.

Pulmonary drug delivery can itself be achieved by different approaches, including liquid nebulizers, aerosol-based metered-dose inhalers (MDI's) and dry powdered dispersion devices. Chlorofluorocarbon (CFC) based MDI's are losing favor because of their adverse effect on the environment. Dry powder dispersion devices, which do not rely on CFC aerosol technology, are promising for delivering drugs that may be readily formulated as dry powders. Many otherwise labile macromolecules may be stably stored as lyophilized or spray dried powders, either by themselves or in combination with suitable powder carriers.

Many pharmaceutical compositions, including antibodies, are quite expensive. Thus, the ability to efficiently formulate, process, package and deliver the dry powders with minimal loss of drug is critical.

An important requirement for hand held and other powder delivery devices is efficiency. It is important that the delivered dose be relatively high to reduce the number of breaths, required to achieve a total dosage. The ability to achieve both adequate dispersion and small dispersed volumes is a significant technical challenge that requires in part that each unit dosage of the powder composition be readily and reliably dispersible. Certain pulmonary delivery devices, such as those disclosed in U.S. Pat. No. 5,797,392, U.S. Pat. No. 5,458,135 and International Patent Publication WO96/09085 are useful for pulmonary delivery of dry powder drugs. Other administration forms of the present composition include liquids, gels, ointments or other suitable formulations for ocular administration, sprays, aerosols, powders, or other compositions for the administration into the nasal cavity, chewing gum, pasta or other compositions for oral cavity, creams, ointments, lotions, gels or other compositions suitable for the application onto the skin, vagitories, gels or other compositions suitable for application onto the vaginal or uro-genital mucosa or formulated as capsules or tablets for the administration into the digestive tract. For dermal application, the polyclonal antibody may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc.

Suitable examples of preservatives for use in compositions are parabenes, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives. Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof. Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

It is normally preferred that a local effect is obtained for the polyclonal antibody. Clearance and thereby activity can be substantially controlled and prolonged by pharmaceutical compositions such as microspheres, liposomes, complexes of positively or negatively charged excipients with antibody molecules of opposite charge.

Therapeutic Uses of Polyclonal Antibodies

In a preferred embodiment, the symphobody included in the present composition is one that reacts with/binds to an inhalant allergen including conjunctival and nasopharyngeal allergens, as well as allergens entering the respiratory tract, or otherwise enters into the body. The preventive or therapeutic inhalation of polyclonal antibodies, e.g. symphobodies, directed against common inhalant allergens is aimed directly at eliminating the cause of the allergy by aiding the blocking, neutralization, and clearance from the respiratory tract of the allergic causative agent before allergic sensitization ensues.

Thus, the present embodiment of the invention concerns the possibility of neutralizing the effect of allergen inhalation via polyclonal antibody inhalations by blocking allergen epitopes otherwise available for the binding of IgE molecules. Also, the binding of polyclonal antibodies is predicted to exert a clearance effect on allergens by mediating the phagocytosis and degradation of allergens without the induction of allergic responses, as well as facilitating the upwards clearance away from the respiratory tract into the pharynx of allergen entrapped in immune complexes with IgA or IgG together with mucosal mucous, and subsequent swallowing into the digestive tract.

Finally, the mucosal administration of allergen-specific polyclonal antibody, e.g. symphobody of the IgG or IgA isotype, which are blocking with respect to the binding of allergen-specific IgE, is hypothesized to inhibit the IgE-mediated antigen presentation for T lymphocytes which may induce the predominantly $T_H2$ type T lymphocyte response to allergens which in allergic individuals is believed to perpetuate the allergy. Instead, the presence of blocking allergen-specific polyclonal antibodies, e.g. symphobodies may result in IgG- or IgA-mediated antigen presentation for T cells, which in turn may preferentially promote a $T_H1$ type T lymphocyte response to allergens, thus interrupting the vicious cycle of the allergic inflammatory reaction.

Allergen epitopes e.g. from pollen are derived from several proteins, and thus for a single inhalant antibody to be able to work, it will be required to contain several if not many individual idiotypic specificities/antigen reactivities. In this respect, polyclonal antibodies seem far superior to monoclonal antibodies.

Consequently, polyclonal antibody compositions may be used for the prophylaxis or treatment of all types of allergy, including allergic rhinitis, hay fever, allergic conjunctivitis, and allergic (extrinsic) asthma, as well as food allergy. In particular, but not limited to, the polyclonal antibody of the present invention is one that reacts with/binds to an allergen from: The house dust mites (e.g. *Dermatophagoides farinae* or *D. pteronyssinus*), danders from cat, dog, or horse; tree pollens from birch (*Betula alba*), alder, hazel, oak, willow, plane, beech, elm, maple, ash, and hornbeam; grass pollens from timothy grass (*Phleum pratense*), bluegrass (*Poa pratense*), rye grass (*Lolium perenne*), Orchard grass (*Dactylis glomerata*), ragweed (e.g. *Ambrosia artemisiifolia*), sweet vernal grass (*anthoxanthum odoratum*), and rye (*Secale cereale*); or fungi (e.g. *Alternaria, Aspergillus, Cladosporium,* and *Penicillium*). In addition, allergen-specific polyclonal antibodies, e.g. symphobodies may be used to treat allergies against other agents such as food allergens (e.g. peanuts and other nuts, shellfish, egg, milk, corn) or bee venom allergens. Many of these allergens may be purchased as well-characterized proteins from commercial suppliers.

The dose of polyclonal antibody required in humans to be effective in the treatment or prevention of allergy differs with the type and severity of the allergic condition to be treated, the type of allergen, the age and condition of the patient, etc. Typical doses of polyclonal antibody to be administered are in the range of 1 μg to 1 g, preferably 1–1000 μg, more preferably 2–500, even more preferably 5–50, most preferably 10–20 μg per unit dosage form.

EXPERIMENTAL

The present invention is described in detail in the following examples which are not in any way intended to limit the scope of the invention as claimed.

Immunization of Mice for the Generation of Symphobody Libraries

BALB/c mice are immunized subcutaneously (s.c.) or intraperitoneally (i.p.) with e.g. 1 mg of allergenic protein in Freunds complete adjuvant. Immunization is performed using recombinant allergen protein (e.g. Der p 1) or extracts from native allergens. Any subsequent immunizations are given at two to three week intervals and in incomplete Freunds adjuvant. Spleen and/or bone marrow are taken 3 days after the last immunization and used for the preparation of the symphobody library, as described in U.S. Pat. No. 5,789,208.

Generation of Symphobody Libraries from Allergic Patient Material

Symphobody libraries are prepared from blood or bone marrow samples taken from allergic patients characterized by positive case history, skin prick testing, radioallergosorbent test (RAST), or reactivity of patient sera with allergen extracts by IgG or IgE immunoblotting or reactivity to purified recombinant allergens (e.g. pollen allergens or animal allergens).

Antibody Binding to Allergen is Detected by ELISA

Between 50 and 1000 ng of allergen, disintegrated allergen, or recombinant allergen are coated pr well of Nunc Maxisorp 96-well microtiter plates. After washes in PBS containing gelatin or BSA as well as Tween-20 the wells are blocked 1 hour at 37° C. using gelatin or BSA. Subsequently the wells are washed and incubated with either polyclonal antibodies, e.g. symphobodies, murine or human IgE, IgG derived from either serum or bronchoalveolar ravages (BAL). After repeated rounds of washing, bound antibody is detected by successive incubations of secondary biotinylated anti-mouse or anti-human immunoglobulin as appropriate, followed by AP-avidin, and pNPP substrate. Previously characterized allergen-specific monoclonal antibodies are used as a positive control and monoclonal and polyclonal antibodies with different, unrelated specificities are used as negative controls.

In some experiments polyclonal antibody incubations are preceded by incubations with well-characterized monoclonal antibodies in a competitive ELISA.

Polyclonal Antibody Inhibition of Binding of Patient-Derived IgE to Allergens

Patient-derived IgE binding to allergen extracts is studied either in competitive ELISA (similar to the protocol above with the following modifications) for IgE binding or by preparative SDS-PAGE and Western blotting. After ELISA well coating or allergen electrophoresis using allergen, disintegrated allergen, or recombinant allergen, the allergen-coated surface is blocked with gelatin or BSA, before incubation 34 hours at 4° C. with allergen-specific polyclonal antibodies. Subsequently, samples are incubated 34 hours at 4° C. with patient sera or BAL IgE diluted 1:5 and bound human IgE antibodies are detected with e.g. $^{125}$I-labeled anti-human IgE antibodies (RAST; Pharmacia) and visualized by autoradiography. Binding of mouse IgG is detected as described above.

Characterization of Polyclonal Antibody Reactivity with Allergen Extracts by Electrophoresis and Western Blotting Allergen extracts are separated by SDS-PAGE and immunoblotted onto nitrocellulose strips before incubation with the antibody preparation (patient sera, mouse sera, polyclonal antibodies, e.g. symphobodies, or control monoclonal antibodies). In some experiments, the cross-reactivity of polyclonal antibodies generated against one allergen is examined by testing in ELISA or Western blotting against a panel of homologous allergens.

Inhibition of Allergen-Induced Histamine Release from Human Basophile Granulocytes After Preincubation of Allergens with Polyclonal Antibodies Heparinized blood samples are obtained from allergic patients and granulocytes isolated by dextran sedimentation.

Recombinant allergens, disintegrated allergens or allergen extracts are preincubated with allergen-specific polyclonal antibodies, e.g. symphobodies, or control antibodies or buffer alone, for 1 h at room temperature before incubation at different concentrations (1, 0.1, 0.01, and 0.001 µg/ml) with granulocytes disintegrated in histamine release buffer (20 mM PIPES, pH 7.4, 110 mM NaCl, 5 mM KCl, 1 mM $CaCl_2$, 1 g/L glucose, 0.3 mg/ml human serum albumin). Histamine release into the cell-free supernatant is determined by radioimmunoassay and expressed as a percentage of total histamine release after cell lysis.

Polyclonal Antibody Inhibition of Allergic Inflammation in a Mouse Model of Allergy Mice (e.g. BALB/c mice, are sensitized to allergens (e.g. ragweed allergen) by two or more i.p. injections of allergen (e.g. 150 microgram) and alum on e.g. days 0 and 4. On e.g. day 11 and in a two to four week timespan, an intratracheal or intranasal allergen challenge is performed on anesthetized mice where after mice are analyzed as described below. In some experiments a mouse model based on ovalbumin (OVA)-sensitization is employed. Briefly, BALB/c mice are injected i.p. with e.g. 5–100 µg OVA (chicken egg albumin grade V, Sigma) in 2 mg aluminum hydroxide adjuvant (alum, Pierce) on day 1 and day 14, before challenge on protocol days 28, 29 and 30 with either 1% aerosolized OVA in PBS for 20 minutes using a ultrasonic nebulizer (DeVilbiss Somerset, Pa. USA) or 5–100 µg OVA in 40 µL PBS injected intratracheally in anesthetized mice. Control mice receive the same amount of PBS.

On day 32, 24 hours after antigen challenge, 12 mice are subjected to an airway responsiveness test and killed on day 33. In the control group B mice are used. The left lung is tied of and BAL of the right lung is obtained by 5 repeated washings with 200 µL PBS. The left lung is fixed and embedded in paraffin for lung histology. A blood sample (tail blood) is also taken from each mouse and stored at –80° C. until analysis is carried out.

In experiments where the ability of allergen-specific polyclonal antibodies, e.g. symphobodies to inhibit allergic inflammation is examined, the allergen-specific polyclonal antibody preparation in doses varying from 1 µg to 1 mg is administered before, during, or after the administration of the challenge dose of antigen.

Polyclonal antibodies with different or unrelated specificities as well as PBS is used as a negative control, and the effect is in some experiments compared with a positive control allergen-specific monoclonal antibody.

Efficacy Evaluation of Polyclonal Antibodies in Blocking the Allergic Response in the Murine Allergy Model Upon completion of the allergen challenge, the allergic reaction is evaluated by performing bronchial lavage (BAL) on euthanized mice, and the BAL fluid is examined by differential counting for the content of eosinophils, neutrophils, lymphocytes, and macrophages.

The lower and upper lobes of the left lung are collected and fixed in Carnoy's solution (6× ethanol; 3× acetic acid glacial; 1× chloroform) at 20° C. for ~15 hours. After embedding in paraffin the tissues are cut into 4–5 µm sections. From each mouse 10 airway sections randomly distributed are assessed for severity of the cellular inflammation and mucus occlusion. The cellular infiltrate of the peribronchial and perivascular areas is evaluated semi-quantitatively for the presence of leukocytes (eosinophils, lymphocytes), quantified on a scale from 0–5 with an increment of 0.5. Mucus occlusion of the bronchial lumen is assigned a score using the following measures 0, 0–10% occlusion; 1, 10–30% occlusion; 2. 30–60% occlusion; 3, 60–90% occlusion; 4, 90–100% occlusion. Damage to the airway epithelium is also estimated on an equivalent scale. All evaluations are performed by individuals blinded to the protocol design and the results are recorded photographically. The tissue sections are stained with hematoxylin and eosin for cellular staining or hematoxylin and periodic acid-Schiff for mucus staining.

Total and OVA-specific IgE, IgG, IgG, $IgG_{2a}$ and $IgG_3$ levels in the blood of mice are determined by ELISA as described above.

What is claimed is:

1. A pharmaceutical composition comprising as an active ingredient an antibody, wherein said antibody is a recombinant polyclonal antibody capable of reacting with or binding to proteins or epitopes derived from an inhaled, ingested, or airborne allergen and wherein said polyclonal antibody is limited to one or more of an IgG, an IgM, an IgA, and an IgD, together with one or more pharmaceutically acceptable excipients, wherein said pharmaceutical composition is free of the allergen to which said recombinant polyclonal antibody is reactive or binds.

2. A pharmaceutical composition according to claim 1, comprising at least one pharmaceutically acceptable excipient capable of effecting topical application of said recombinant polyclonal antibody.

3. A pharmaceutical composition according to claim 1, which is intended for topical administration to the oropharynx, nasal cavity, respiratory tract, gastrointestinal tract, conjunctival mucosa, vagina, urogenital mucosa, or for dermal application.

4. A pharmaceutical composition according to claim 3, wherein the respiratory tract is selected from nasal, oral, pharyngeal, bronchial, or alveolar mucosa.

5. A pharmaceutical composition according to claim 1, which is provided as a solution, dispersion, powder or in the form of microspheres.

6. A pharmaceutical composition according to claim 1, wherein the recombinant polyclonal antibody is generated by phage display technology.

7. A pharmaceutical composition according to claim 6, wherein the recombinant polyclonal antibody is generated under such conditions that the immunoglobulin heavy chain variable region and light chain variable region gene segments are linked together in a parental library in order to allow for the bulk transfer of variable region light chain and heavy chain gene pairs from one vector to another, while allowing stable pairing of specific immunoglobulin variable region light chain and heavy chain gene segments as they are present upon selection from the parental library of immunoglobulin variable region light chain and heavy chain gene segment pairs encoding antibody molecules capable of reacting with or binding to an allergen.

8. A pharmaceutical composition according to claim 6, wherein the recombinant polyclonal antibody is generated under such conditions that the immunoglobulin heavy chain variable region and light chain variable region gene segments are linked together in order to allow for the bulk transfer of specific variable region light chain and heavy chain gene pairs from one vector to another, while allowing stable pairing of specific immunoglobulin variable region light chain and heavy chain gene segments as they are present in the original polyclonal immune response of an animal or human individual.

9. A pharmaceutical composition according to claim 1, wherein the allergen is an allergen of house dust mites, dander from cat, dander from dog, dander from horse, tree pollen, grass pollen, or fungi.

10. A pharmaceutical composition according to claim 1, comprising the recombinant polyclonal antibody in an amount in the range of 1 µg to 1 g per unit dosage form.

11. A pharmaceutical composition according to claim 1, wherein said polyclonal antibody is an IgG antibody.

12. A pharmaceutical composition according to claim 1, wherein said polyclonal antibody is an IgM antibody.

13. A pharmaceutical composition according to claim 1, wherein said polygonal antibody is an IgA antibody.

14. A pharmaceutical composition according to claim 1, wherein said polyclonal antibody is an IgD antibody.

15. A pharmaceutical composition according to claim 1, wherein said polyclonal antibody has antibody molecules from a mixture of antibody classes.

16. A pharmaceutical composition according to claim 1, wherein said polyclonal antibody binds said allergen with sufficient density to mediate the elimination of said allergen from a patient.

17. A pharmaceutical composition according to claim 1, wherein said polyclonal antibody binds said allergen with a higher antibody density than a monoclonal antibody.

18. A pharmaceutical composition according to claim 1, wherein said polyclonal antibody does not cross-react with endogenous self-antigens in a patient.

19. A pharmaceutical composition according to claim 1, wherein said polyclonal antibody does not elicit an anaphylactic response in humans.

20. A pharmaceutical composition according to claim 1, wherein said polyclonal antibody is a fully human antibody.

21. A pharmaceutical composition according to claim 1, wherein the variable region of said polyclonal antibody has a mutation.

22. A pharmaceutical composition according to claim 1, wherein at least 85% of the antibody molecules in said composition are target-specific.

23. A pharmaceutical composition according to claim 1, wherein at least 90% of the antibody molecules in said composition are target-specific.

24. A pharmaceutical composition according to claim 1, wherein said polyclonal antibody is a complete antibody molecule or fragment thereof such as an $F_{ab}$ fragment.

25. A pharmaceutical composition according to any claim 1, wherein said composition is provided as a microsphere, liposome, polyethylene glycol-conjugated complex, or complex of positively or negatively charged excipients with antibody molecules of the opposite charge, wherein said composition prolongs the clearance of said polyclonal antibody in a patient.

* * * * *